United States Patent
Mizuochi et al.

(10) Patent No.: US 9,523,631 B2
(45) Date of Patent: Dec. 20, 2016

(54) LOAD DETECTING DEVICE AND WORKING MACHINE PROVIDED WITH SAME

(71) Applicant: Hitachi Construction Machinery Co., Ltd., Bunkyo-ku, Tokyo (JP)

(72) Inventors: Mariko Mizuochi, Tokyo (JP); Akinori Ishii, Tsuchiura (JP)

(73) Assignee: Hitachi Construction Machinery Co., Ltd., Tokyo (JP)

( * ) Notice: Subject to any disclaimer, the term of this patent is extended or adjusted under 35 U.S.C. 154(b) by 0 days.

(21) Appl. No.: 14/773,087

(22) PCT Filed: Jul. 3, 2014

(86) PCT No.: PCT/JP2014/067820
§ 371 (c)(1),
(2) Date: Sep. 4, 2015

(87) PCT Pub. No.: WO2015/005225
PCT Pub. Date: Jan. 15, 2015

(65) Prior Publication Data
US 2016/0011090 A1    Jan. 14, 2016

(30) Foreign Application Priority Data
Jul. 9, 2013   (JP) ................. 2013-143795

(51) Int. Cl.
*G01N 3/24*   (2006.01)
*G01G 3/14*   (2006.01)
(Continued)

(52) U.S. Cl.
CPC .............. *G01N 3/24* (2013.01); *G01G 3/1408* (2013.01); *G01L 1/18* (2013.01); *G01L 1/2293* (2013.01); *G01L 5/0061* (2013.01); *G01G 19/12* (2013.01)

(58) Field of Classification Search
CPC ........................................................ G01N 3/24
(Continued)

(56) References Cited

U.S. PATENT DOCUMENTS 3,695,096 A * 10/1972 Kutsay ................. G01L 1/2225
73/761
4,454,769 A    6/1984 Loos
(Continued)

FOREIGN PATENT DOCUMENTS

JP   57-157129 A   9/1982
JP    59-75123 A   4/1984
(Continued)

OTHER PUBLICATIONS

International Search Report (PCT/ISA/210) dated Aug. 5, 2014, with English translation (four (4) pages).

*Primary Examiner* — Lisa Caputo
*Assistant Examiner* — Octavia Hollington
(74) *Attorney, Agent, or Firm* — Crowell & Moring LLP

(57) ABSTRACT

A load detecting device that can highly accurately detect the magnitude and direction of a load whose direction of action changes regardless of the dimension of a pin is provided. Also, a working machine that is provided with this load detecting device and allows work to be performed safely and highly efficiently is provided. The load detecting device is configured with a pin-type load cell 4 and a load calculating unit 30. The pin-type load cell 4 is provided with three pairs of or three strain detecting units that are placed in the circumferential direction of the pin body 1. The load calculating unit 30 selects, from among the three or more pairs of or three or more strain detecting units, two pairs of or two strain detecting units that are less influenced by a change in the cross-sectional shape of the pin body 1, and calculates a (Continued)

load that acts on the pin body 1 according to an output of these selected strain detecting units.

9 Claims, 11 Drawing Sheets

(51) Int. Cl.
    *G01L 1/18*     (2006.01)
    *G01L 1/22*     (2006.01)
    *G01L 5/00*     (2006.01)
    *G01G 19/12*     (2006.01)

(58) Field of Classification Search
    USPC .......................................................... 73/841
    See application file for complete search history.

(56) References Cited

U.S. PATENT DOCUMENTS

| | | | |
|---|---|---|---|
| 5,507,187 A | | 4/1996 | Miyazaki |
| 5,910,645 A | * | 6/1999 | Gerlach .................. G01L 1/26 177/1 |
| 7,793,551 B2 | * | 9/2010 | Shimazu .................. G01L 1/18 73/760 |

FOREIGN PATENT DOCUMENTS

| | | |
|---|---|---|
| JP | 6-241922 A | 9/1994 |
| JP | 2010-107266 A | 5/2010 |
| JP | 2010-159548 A | 7/2010 |
| JP | 2010-281783 A | 12/2010 |

\* cited by examiner

LOAD DETECTING DEVICE AND WORKING MACHINE PROVIDED WITH SAME

TECHNICAL FIELD

The present invention relates to a load detecting device comprising a pin-type load cell, and a working machine comprising the load detecting device.

BACKGROUND ART

It is important to detect a load that each machine piece that configures a machine receives, in grasping the state of the machine and in performing drive control of the machine. Conventionally, as a load detecting device that detects a load that acts on a coupling pin of mechanism members combined into a link, one that uses a pin-type load cell in which a load detection function is provided to the coupling pin itself of the mechanism members has been known. The pin-type load cell is inserted into a coupling unit of mechanism members, and detects a load that acts on the coupling unit.

It is essential, in a working machine such as a hydraulic excavator, to measure a load that acts on an attachment part in order to grasp a work amount and ensure safety. Patent Literature 1 proposes, as a pin-type load cell that is suitable for this type of a working machine, one that is provided with a pin hole provided in the axial direction of a pin, and with two strain sensors that are positioned on the same circumference in the wall surface of this pin hole or the outer periphery of the pin, and are mounted on two mutually orthogonal surfaces, one strain sensor for each surface, and has a value of the diameter of the pin hole/the outer diameter of the pin of 0.2 or smaller. Because the pin-type load cell described in Patent Literature 1 prevents deformation of the cross-sectional shape of the pin due to a load by controlling the diameter of the pin hole, it is possible to measure a load that acts on the pin highly accurately even when the direction of action of the load changes.

CITATION LIST

Patent Literature

Patent Literature 1: JP-A No. 2010-159548

SUMMARY OF INVENTION

Technical Problem

However, because the pin-type load cell described in Patent Literature 1 defines the hole diameter of the pin relative to the outer diameter of the pin as being 0.2 or smaller, it has problems in that it is difficult to sufficiently ensure a joining surface of a strain sensor in a pin hole for a pin-type load cell that has a small outer diameter of a pin and in which the strain sensor is mounted in the pin hole, and the measurement accuracy is constrained by the dimension of the pin.

The present invention has been made to solve the above-described problems, and an object thereof is to provide a load detecting device that can highly accurately detect the magnitude and direction of a load whose direction of action changes regardless of the dimension of a pin, and a working machine that is provided with this load detecting device and allows work to be performed safely and highly efficiently.

Solution to Problem

In order to solve the above-described problems, the present invention is characterized in that a load detecting device comprises: a pin-type load cell; and a load calculating unit that calculates a load that acts on the pin-type load cell according to a detection signal output of the pin-type load cell, wherein the pin-type load cell includes a pin body provided with a pin hole in an axial direction, and three or more pairs of or three or more strain detecting units placed in a circumferential direction of the pin body, and the load calculating unit includes a selecting unit that selects, from among the three or more pairs of or three or more strain detecting units, a strain detecting unit that is less influenced by a change in a cross-sectional shape of the pin body, and a calculating unit that calculates a load that acts on the pin body based on a detection signal output of the strain detecting unit selected by the selecting unit.

The cross-sectional shape of a pin having a pin hole is deformed vertically asymmetrically relative to the direction of action of a shearing load, when the load is applied. Also, a load whose direction of action changes from moment to moment along with the progress of work acts on a turning shaft (pin) that couples an arm and an attachment of a working machine. For this reason, when it is attempted, as in the pin-type load cell according to the conventional example, to detect a load that acts on the coupling unit of the arm and the attachment of the working machine by using the pin-type load cell on which strain sensors are mounted on two mutually orthogonal surfaces, one strain sensor for each surface, the strain amount attributable to deformation of the cross-sectional shape of the pin may be superimposed on a detection signal of the pin-type load cell depending on the direction of action of the load, and it is not possible to detect the load accurately. To cope with this, because by providing the three or more pairs of or three or more strain detecting units in the circumferential direction of the pin (pin body), it is possible, when performing load detection, to select strain detecting units that are less influenced by deformation of the cross-sectional shape of the pin as appropriate, and calculate a load that acts on the pin, it is possible to detect the load that acts on the pin accurately even when the cross-sectional shape of the pin having the pin hole is deformed vertically asymmetrically due to the load being applied. Therefore, it is not necessary to regulate pin hole sizes, and it is possible to perform load detection of a wide range of parts with different pin sizes.

Also, the present invention is characterized in that in the load detecting device with the configuration, the strain detecting unit detects a shearing strain at a mounting location.

The pin-type load cell is used to detect a load that act on a coupling unit of a link member, and shearing force acts on the coupling unit of the link member. Accordingly, by using, as the strain detecting unit, one that detects shearing strain at the mounting location, it is possible to detect a load that acts on the coupling unit of the link member accurately.

Also, the present invention is characterized in that in the load detecting device with the configuration, the three or more pairs of strain detecting units are each a pair of two strain sensors placed at opposite positions via a shaft center of the pin body.

Because by configuring a strain detecting unit to form a pair of two strain sensors that are placed at opposite positions via the shaft center of the pin body, it is possible to cancel out influence of a bending moment that acts on the pin body by obtaining a difference between detection signal outputs of these two strain sensors, it is possible to detect shearing force that acts on the pin body accurately.

Also, the present invention is characterized in that in the load detecting device with the configuration, another at least one pair of or one strain detecting unit is set at a position that is 90° or more away from a setting position of a particular one pair of or one strain detecting unit from among the three or more pairs of or three or more strain detecting units.

By installing another at least one pair of or one strain detecting unit at a location that is 90° or more away from a setting position of a particular one pair of or one strain detecting unit without concentrating three or more pairs of or three or more strain detecting units at one quadrant in the circumferential direction of a pin, it is possible to select strain detecting units that are less influenced by deformation of the cross-sectional shape of the pin, and have sufficient outputs even when a load acts from any direction, and to detect the load more highly accurately.

Also, the present invention is characterized in that in the load detecting device with the configuration, the load calculating unit selects, from among the three or more pairs of or three or more strain detecting units, two pairs of or a group of two strain detecting units that bring about a smallest load calculated value, and calculates loads that act in an x-axis direction and a y-axis direction that is orthogonal thereto of the pin body according to detection signal outputs of the selected two pairs of or two strain detecting units.

If a strain sensor calibration result obtained by using loads at a setting position of particular one pair of or one strain detecting unit and a setting position that is orthogonal thereto is used, a load detection value attributable to vertically asymmetric deformation of the pin body is always a positive value. Accordingly, by selecting two pairs of or a group of two strain detecting units that bring about the smallest load calculated value to calculate a load, a detection error attributable to changes in the tendency in the cross-section of the pin body can be minimized.

Also, the present invention is characterized in that in the load detecting device with the configuration, the load calculating unit selects, from among the three or more pairs of or three or more strain detecting units, a strain detecting unit that is less influenced by a change in a cross-sectional shape of the pin body by using information on a direction of action of a load, and calculates a load according to an output of the selected strain detecting units.

Because by using the direction of action of a load, it is possible to derive a relationship between each strain detecting unit and the direction of action of the load, and to find a strain detecting unit that is less influenced by a change in the cross-sectional shape of a pin body, load calculation that is less influenced by the change in the cross-sectional shape of the pin body can be performed by selecting it.

Also, the present invention is characterized in that in the load detecting device with the configuration, the load calculating unit selects two pairs of or two strain detecting units whose angles relative to the direction of action of the load are farthest from 45°, 135°, 225° and 315°, and calculates the load that acts on the pin body based on a detection signal output of the selected two pairs of or two strain detecting units.

Influence of the change in the cross-sectional shape of the pin body becomes largest when the angles formed between the direction of action of a load and a strain detecting unit is 45°, 135°, 225° and 315°. Accordingly, by selecting two pairs of or two strain detecting units whose angles relative to a direction of action of the load are farthest from 45°, 135°, 225° and 315°, and calculating a load that acts on the pin body, highly accurate load detection can be performed.

Also, the present invention is characterized in that in a working machine, a coupling unit of a mechanism member is joined by using the pin-type load cell according to any one of Claims 1 to 7.

A load whose magnitude and direction change from moment to moment along with the progress of work acts on the coupling unit of the mechanism member that configures the working machine. As mentioned above, because the pin-type load cell according to any one of Claims 1 to 7 can perform load detection highly accurately even when the cross-sectional shape of the pin body has changed due to such a load being applied, it is possible to aim for enhancement of work efficiency while enhancing safety of work.

Also, the present invention is characterized in that the working machine with the configuration comprises: a undercarriage; an upperstructure mounted on an upper portion of the undercarriage; a working device mounted freely turnably on the upperstructure; an attachment mounted on a tip of the working device via a turning shaft; a posture detecting unit that detects a posture of the working machine; an arithmetic operation device that performs arithmetic operation to determine a load that acts on the attachment; and a display device that displays the load that acts on the attachment, wherein: a coupling unit between the working device and an attachment is coupled by using the pin-type load cell; the arithmetic operation device calculates a load applied to the attachment based on an output of the posture detecting unit and the pin-type load cell; and the display device displays magnitude and a direction of a load based on an output result of the arithmetic operation device.

By coupling a coupling unit between a working device and an attachment by using the pin-type load cell, it is possible to highly accurately detect a load that acts on the coupling unit between the working device and the attachment regardless of a change in the direction of action of the load for the working machine provided with an attachment such as a hydraulic excavator, for example. Also, because the arithmetic operation device calculates a load applied to the attachment based on outputs of the posture detecting unit and the pin-type load cell that are provided at each portion of the working machine, it is possible to accurately grasp the direction of a load that acts on the attachment. Furthermore, because a result of calculating a load is displayed on the display device, an operator of the working machine can clearly recognize a load that acts on the attachment at any time, and it is possible to aim for safety of work and enhancement of work efficiency.

Effect of Invention

According to the present invention, even when the direction of a load that acts on a pin body configuring a pin-type load cell changes, the magnitude and direction of the load that acts on the pin body can be detected highly accurately with a simple configuration that is not constrained by the dimension of the pin body.

BRIEF DESCRIPTION OF DRAWINGS

FIGS. 11A and 11B are figures for showing a load calculated value of a pin-type load cell according to a conventional example, in which FIG. 11A is a graph in which the orientation of a straight line passing through the origin O corresponds to a load direction and the distance from the origin O corresponds to a load measured value, and FIG. 11B is a graph whose horizontal axis corresponds to the load direction and whose vertical axis corresponds to the load measured value.

FIGS. 12A and 12B are figures for showing a pin-type load cell according to an embodiment, in which FIG. 12A is a figure that shows Fab, Fac, and Fbc obtained when the direction in which a load acts is changed in a pin-type load cell 4 according to an embodiment, and FIG. 12B is a figure that shows a load calculated value Fabc.

DESCRIPTION OF EMBODIMENTS

Working Machine

First, an embodiment of a working machine according to the present invention is explained with reference to FIG. 1 to FIG. 3.

<External Appearance Configuration of Working Machine>

Figure 1:
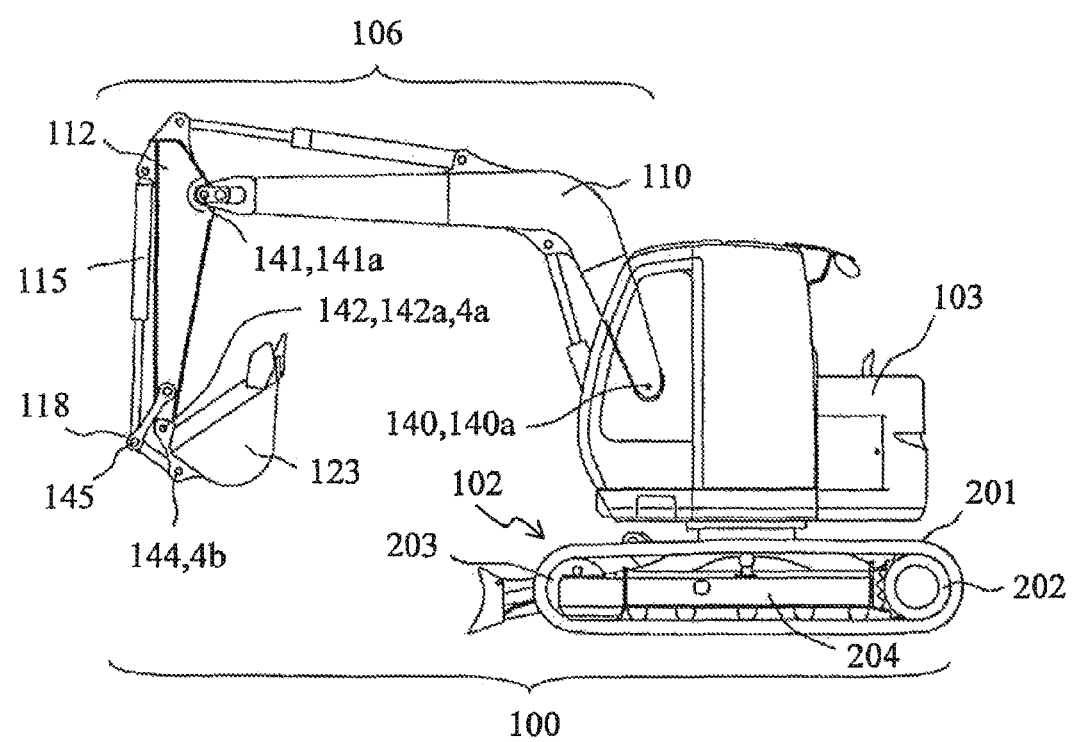
FIG. 1 is a side view of a working machine according to an embodiment.

As shown in FIG. 1, a working machine 100 according to an embodiment is mainly configured with: a undercarriage 102 that travels while being in contact with the ground; an upperstructure 103 mounted on the undercarriage 102; and a working device 106 one end of which is turnably mounted on the upperstructure 103.

The undercarriage 102 described in FIG. 1 is a so-called crawler type, and is configured with: a crawler 201 that contacts the ground; a driving wheel 202 that drives the crawler 201; a driven wheel 203 that is rotated by the crawler 201; a structure 204 that supports them, and the like. It should be noted that the undercarriage 102 may be configured as a so-called wheel type comprising a plurality of wheels.

The upperstructure 103 is mounted on an upper portion of the undercarriage 102. The working machine 100 in the present example is a hydraulic excavator, and the upperstructure 103 is mounted on the undercarrige 102 via a swing device or not via a swing device.

The working device 106 is also called a working front, and is mounted before the upperstructure 103 as seen from an operator's cab. In the example of FIG. 1, a boom 110 mounted on the upperstructure 103 so as to be freely turnable only in the up-down direction via a turning shaft 140, an arm 112 mounted on the tip of the boom 110 so as to be freely turnable only in the up-down direction via a turning shaft 141, and an attachment 123 mounted on the tip of the arm 112 so as to be freely turnable only in the up-down direction via a turning shaft 142 are mounted on the working device 106.

In the example of FIG. 1, a bucket is mounted on the tip of the arm 112 as the attachment 123, and one end of a link mechanism 118 whose another end is coupled with the arm 112 is coupled with the attachment (the bucket) 123 via a turning shaft 144. Also, the rod-side end portion of an attachment cylinder 115 whose one end is mounted on the arm 112 is coupled with the link mechanism 118 via a turning shaft 145. The attachment cylinder 115 is a hydraulic cylinder, and extends and contracts to turn the attachment 123 about the turning shaft 142. It should be noted that another attachment such as a grapple, cutter, breaker, magnet or the like can be mounted in place of the bucket depending on work.

Figure 2:
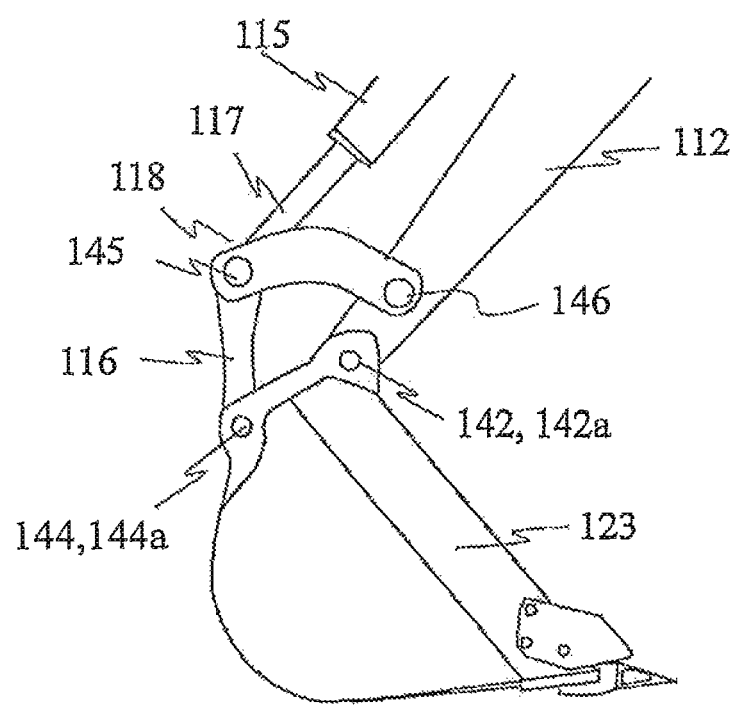
FIG. 2 is an enlarged side view of an attachment peripheral part of a working machine according to an embodiment.

FIG. 2 is a detailed view of a peripheral part of the attachment 123. As is obvious from this figure, the link mechanism 118 shown in FIG. 1 has a first link 116 that is bridged between the rod-side tip portion of the attachment cylinder 115 and the attachment 123, and a second link 117 that is bridged between the rod-side tip portion of the attachment cylinder 115 and the arm 112. The first link 116 is mounted turnably on the attachment 123 via the turning shaft 144 at one end portion, and is mounted turnably on the attachment cylinder 115 via the turning shaft 145 at the other end portion. On the other hand, the second link 117 is mounted turnably on the arm 112 via a turning shaft 146 on one end portion, and is mounted turnably on the attachment cylinder 115 via the turning shaft 145 at the other end portion. It should be noted that the link mechanism 118 may be one that has another configuration. For example, a link mechanism with four joints that is configured by adding, to the link mechanism 118 of FIG. 2, a third link member that is bridged between the rod-side tip portion of the attachment cylinder 115 and the turning shaft 145, and a fourth link member that is bridged between the rod-side tip portion of the attachment cylinder 115 and the arm 112 may be provided. Furthermore, one that has a combination of four or more link members may be used.

<State Quantity Detecting Unit of Working Machine>

A sensor for detecting a state quantity of a working machine (state quantity detecting unit) is provided to a required part of the machine. In the following, a state quantity detecting unit provided to the working machine 100 according to an embodiment is explained by referring to FIG. 1 to FIG. 3. The state quantity detecting unit of the working machine 100 is configured with a posture detecting device that detects a posture of the attachment 123, and a load detecting device that detects a load applied to the attachment 123.

<Posture Detecting Device>

As shown in FIG. 1, the working machine 100 is provided with, as the posture detecting device to detect a posture of the attachment 123, a boom angle sensor 140a, an arm angle sensor 141a, and an attachment angle sensor 142a. The boom angle sensor 140a detects a rotation angle (relative angle) of the boom 110 relative to the upperstructure 103, and is provided to the turning shaft 140 of the upperstructure 103 and the boom 110. The arm angle sensor 141a detects a rotation angle (relative angle) of the arm 112 relative to the boom 110, and is provided to the turning shaft 141 of the boom 110 and the arm 112. The attachment angle sensor 142a detects a rotation angle (relative angle) of the attachment 123 relative to the arm 112, and is provided to the turning shaft 142 of the arm 112 and the attachment 123. In the working machine 100, an arithmetic operation device 160 described below calculates an absolute angle θ (angle relative to the ground) of the posture of the attachment 123 relative to the horizontal plane based on detection values of the boom angle sensor 140a, the arm angle sensor 141a, and the attachment angle sensor 142a.

<Load Detecting Device>

Also, the working machine 100 has, as load detecting devices to detect a load applied to the attachment 123, pin-type load cells 4a, 4b that detect loads in two axial directions that are orthogonal to each other. The pin-type load cells 4a, 4b are provided in place of coupling pins provided to the turning shaft 142 and the turning shaft 144. By providing strain detecting units to the pin bodies formed into required shapes and sizes corresponding to the turning shafts 142, 144, the pin-type load cells 4a, 4b are able to detect force that acts on the pin bodies. The specific configuration of the pin-type load cells 4a, 4b is explained in detail below by using FIG. 6 and FIG. 7. The pin-type load cell 4a is fixed to the attachment 123 at a setting position of the turning shaft 142 so as to turn together with the attachment 123. On the other hand, the pin-type load cell 4b is fixed to the attachment 123 at a setting position of the turning shaft 144 so as to turn together with the attachment 123.

Figure 3:
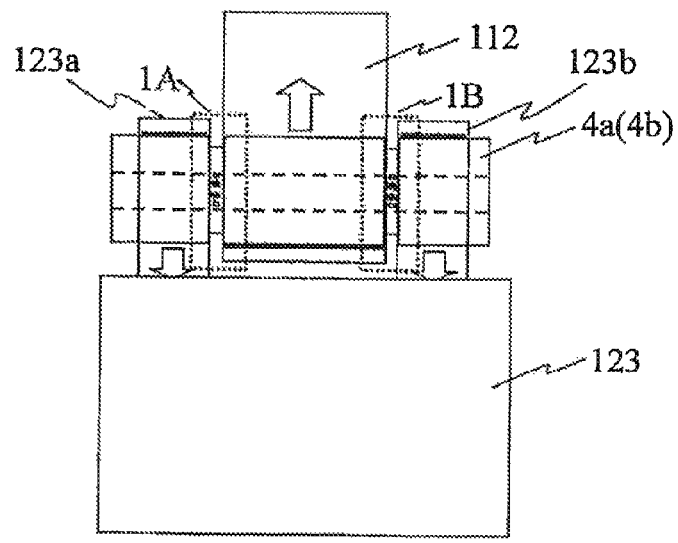
FIG. 3 is an enlarged front view of the attachment peripheral part of a working machine according to an embodiment.

As shown in FIG. 3, in the attachment 123, two ribs 123a, 123b for coupling the arm 112 via the turning shafts 142, 144 are formed to face each other with a required interval therebetween. The tip portion of the arm 112 is placed between the two ribs 123a, 123b, and by causing the pin-type load cells 4a, 4b as substitutes of coupling pins corresponding to the turning shafts 142, 144 to penetrate through a through-hole opened at the tip portion of the arm 112 and through-holes opened in the two ribs 123a, 123b, the attachment 123 is mounted freely turnably on the tip portion of the arm 112. Accordingly, when a load such as that of earth and sand is applied to the attachment 123, upward and downward force acts on contact portions between the pin-type load cells 4a, 4b and the arm 112, and contact portions between the pin-type load cells 4a, 4b and the attachment 123, respectively, as indicated with outline arrows in FIG. 3, and shear deformation occurs at shearing strain generating portions 1A, 1B between the arm 112 and the ribs 123a, 123b. For such a reason, those that detect shearing strain occurring at these shearing strain generating portions 1A, 1B are used as the pin-type load cells 4a, 4b.

<Load Measuring Device>

Figure 4:
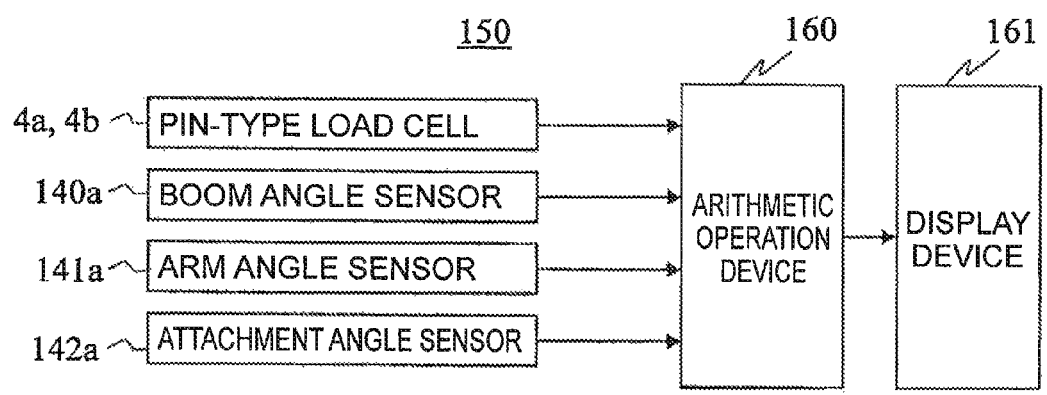
FIG. 4 is a configuration diagram of a load measuring device provided to a working machine according to an embodiment.

FIG. 4 shows the configuration of a load measuring device 150 that measures a load that acts on a coupling unit of the arm 112 and the attachment 123 according to detection signals of the above-mentioned posture detecting device and load detecting device. As is obvious from this figure, the load measuring device 150 in the present example is configured with the two-axis pin-type load cells 4a, 4b, the boom angle sensor 140a, the arm angle sensor 141a, the attachment angle sensor 142a, the arithmetic operation device 160, and a display device 161.

The arithmetic operation device 160 has a central processing unit and a memory unit that are not illustrated, and detects a posture of the attachment 123 based on detection signals of the angle sensors 140a, 141a, 142a and calculates the magnitude and direction of force applied to the attachment 123 based on attachment posture information and detection signals of the pin-type load cells 4a, 4b.

The display device 161 is connected to the arithmetic operation device 160, and displays the magnitude and direction calculated by the arithmetic operation device 160. An operator of the working machine can operate the working machine while referring to the magnitude and direction of force displayed on this display device 161.

Figure 5:
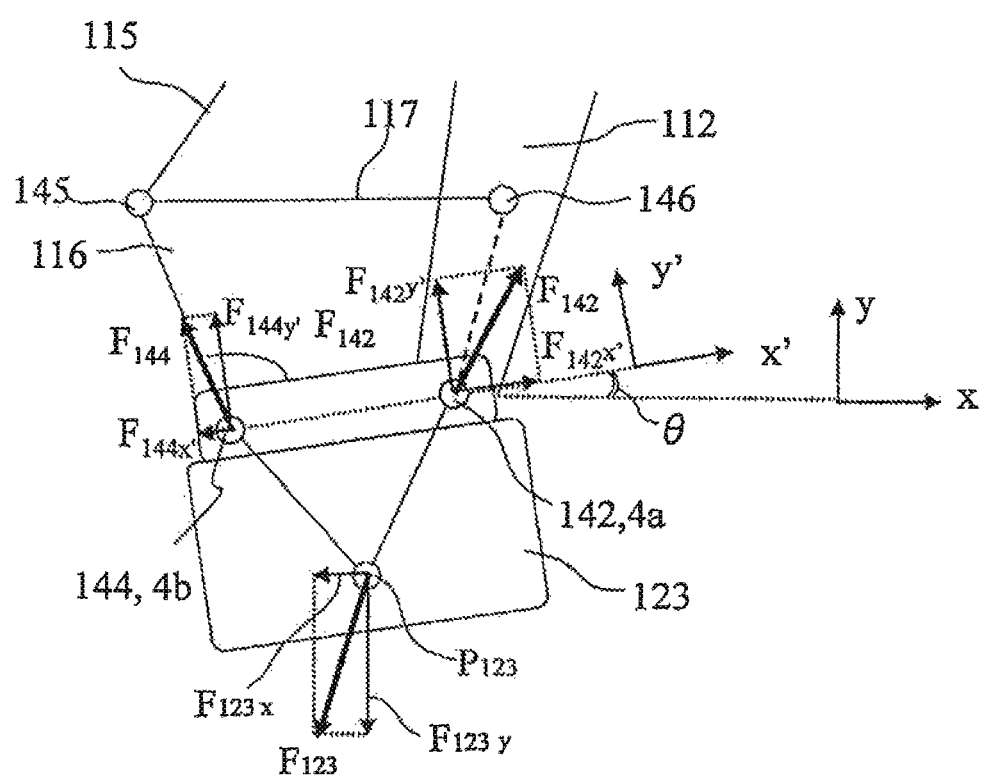
FIG. 5 is a view for showing a method to perform arithmetic operation to obtain a load that acts on an attachment of a working machine according to an embodiment.

In the following, a specific arithmetic operation method performed in the arithmetic operation device 160 is explained by using FIG. 5. FIG. 5 is a diagram showing a relationship between force $F_{123}$ applied to the attachment 123, force $F_{142}$ detected by the pin-type load cell 4a, and force $F_{144}$ detected by the pin-type load cell 4b. As a reference coordinate system, the x-axis and the y-axis are set as the front-back direction and the orthogonal direction of the working machine 100, respectively. Also, as a coordinate system of the attachment 123 (attachment coordinate system), the x'-axis is set in the direction of a line segment that connects the turning shaft 142 and the turning shaft 144, and the y'-axis is set in the direction that is perpendicular to this x'-axis. It is assumed here that, when the force $F_{123}$ acts on a point $P_{123}$ at the attachment 123, the force $F_{142}$ acts on the turning shaft 142, and the force $F_{144}$ acts on the turning shaft 144.

At this time, the pin-type load cell 4a that is provided to the turning shaft 142, and fixed to the attachment 123 detects the force $F_{142}$ that acts on the turning shaft 142 as force $F_{142x'}$ in the x'-axis direction and force $F_{142y'}$ in the y'-axis direction, and outputs them to the arithmetic operation device 160. Similarly, the pin-type load cell 4b that is provided to the turning shaft 144 and fixed to the attachment 123 detects force $F_{144}$ that acts on the turning shaft 144 as force $F_{144x'}$ in the x'-axis direction and force $F_{144y'}$ in the y'-axis direction, and outputs them to the arithmetic operation device 160.

The arithmetic operation device 160 calculates an x'-axis direction component $F_{123x'}$ and a y'-axis direction component $F_{123y'}$ of the force $F_{123}$ that acts on the attachment 123 as follows by using $F_{142x'}$, $F_{142y'}$, $F_{144x'}$, $F_{144y'}$.

[Equation 1]

$$F_{123x'} = F_{142x'} + F_{144x'}$$

$$F_{123y'} = F_{142y'} + F_{144y'} \quad (1)$$

The arithmetic operation device 160 calculates an angle θ (see FIG. 5) of the attachment 123 relative to the horizontal plane (x-axis direction) based on detection values of a boom angle sensor 140a, an arm angle sensor 141a, and an attachment angle sensor 142a (posture detecting devices). Then, the arithmetic operation device 160 calculates an x-axis direction component $F_{23x}$ and a y-axis direction component $F_{123y}$ of the force $F_{123}$ applied to the attachment 123 as follows by using the above-described angle θ and $F_{123x'}$, $F_{123y'}$ calculated according to the above-mentioned equation. Thereby, the arithmetic operation device 160 can calculate the magnitude and direction of the force $F_{123}$ that acts on the attachment 123.

[Equation 2]

$$\begin{bmatrix} F_{123x} \\ F_{123y} \end{bmatrix} = \begin{bmatrix} \cos\theta & -\sin\theta \\ \sin\theta & \cos\theta \end{bmatrix} \begin{bmatrix} F_{123x'} \\ F_{123y'} \end{bmatrix} \quad (2)$$

<Load Detecting Device>

Next, an embodiment of a load detecting device to be applied to the above-mentioned working machine is explained by referring to figures.

<Configuration of Pin-Type Load Cell>

Figure 6:
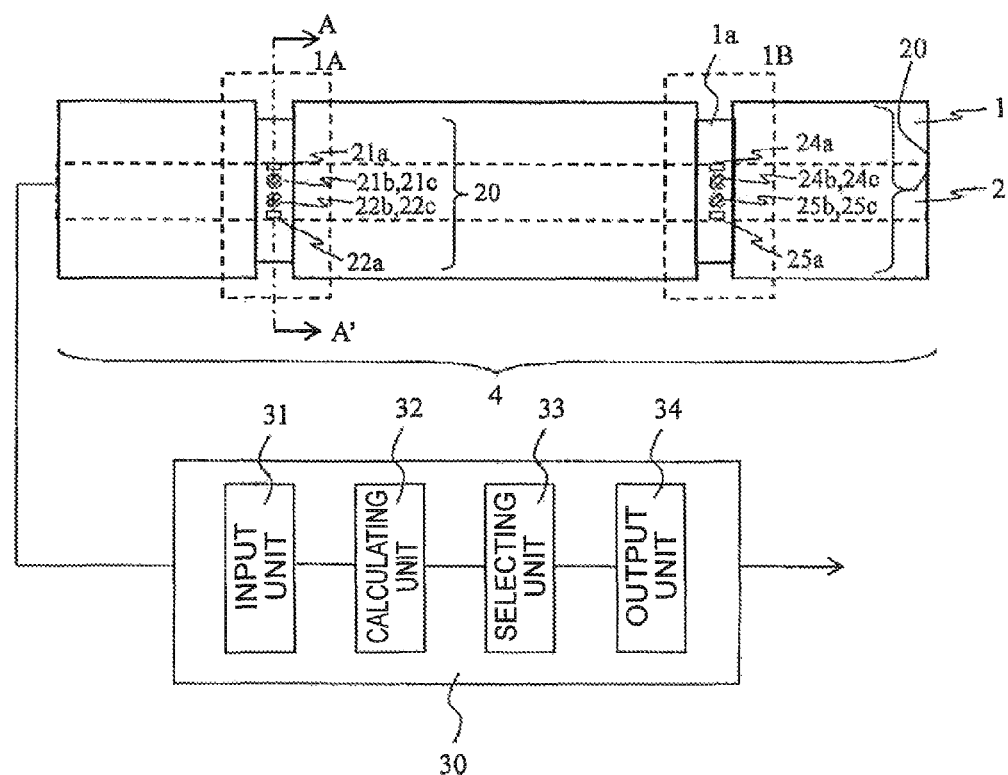
FIG. 6 is a cross-sectional view of a pin-type load cell according to an embodiment.

As shown in FIG. 6, the load detecting device according to the embodiment is configured with a pin-type load cell 4, and a load calculating unit 30 that calculates a load that acts on the pin-type load cell 4 according to a detection signal of the pin-type load cell 4. It should be noted that the pin-type load cell 4 is a generic term of the pin-type load cells 4a, 4b.

Figure 7:
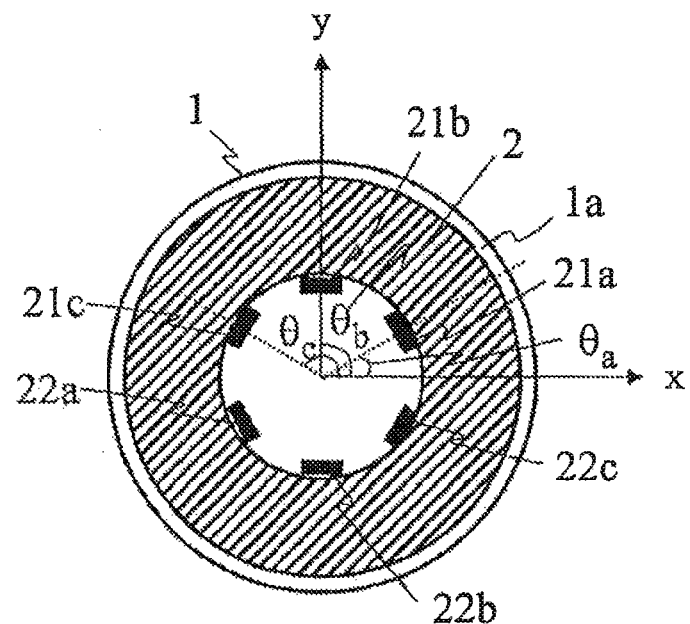
FIG. 7 is a horizontal cross-sectional view of a shear deformation generating portion of a pin-type load cell according to an embodiment.

As shown in FIG. 6, the pin-type load cell 4 consists of a pin body 1 that is formed by using a structural carbon steel such as S45C and has a predetermined dimension, and a shearing strain detecting unit 20 mounted within a pin hole 2 of the pin body 1. The pin hole 2 is a hole provided concentrically with the pin body 1 and in the axial direction of the pin body 1, and may be a through-hole that penetrates through the pin body 1, or may be a semi-through-hole that is provided so as to reach, from both ends of the pin body 1, at least portions that correspond to shearing strain generating portions 1A, 1B of FIG. 3. Concave portions 1a are formed at predetermined positions of the outer periphery of the pin body 1, that is, the portions that correspond to the shearing strain generating portions 1A, 1B described in FIG. 3. As shown in FIG. 6 and FIG. 7, a plurality of strain sensors that configure the shearing strain detecting units 20 are provided to portions that correspond to portions that are inside the pin hole 2 and where the concave portions 1a are formed.

The shearing strain detecting units 20 are configured with a plurality of strain sensors that detect shearing strain that acts on the pin body 1. Metal resist strain gauges that are used generally widely, semiconductor strain sensors that use an impurity diffusion resistor in which impurities are introduced into a monocrystalline silicon substrate, and the like can be used as strain sensors.

In the present embodiment, as shown in FIG. 7, three pairs of strain sensors are placed per single shearing strain generating portion 1A or 1B in the circumferential direction of the pin hole 2, each pair being formed by two pieces of strain sensors that are placed to be opposite to each other. In FIG. 7, strain sensors 21a and 22a configure a pair of strain sensors, strain sensors 21b and 22b configure another pair of strain sensors, and strain sensors 21c and 22c configure a still another pair of strain sensors. The sensor pairs (21a, 22a), (21b, 22b), (21c, 22c) are placed at positions θa, θb, θc from the x-axis, respectively. Strain sensors 24a and 25a, 24b and 25b, 24c and 25c that are set for the other shearing strain generating portion 1B are similarly configured. Each pair of strain sensors detects shearing strain occurring at each sensor mounting position. It should be noted that a reason why three pairs of strain sensors are placed in the circumferential direction of the pin hole 2 is to ensure that even when the cross-sectional shape of the pin body 1 is deformed to be asymmetric about the shaft center due to a load being applied, there are two pairs of strain sensors at positions that are less likely to be influenced by the deformation. Also, a reason why two pieces of strain sensors are placed to be opposite to each other via a shaft center is to remove influence of strain due to a bending moment, and when influence of strain due to a bending moment can be ignored, strain sensors need not be placed in pairs, and three strain sensors placed in the circumferential direction of the pin hole 2 are sufficient.

It should be noted that the above-mentioned angles θa, θb, θc at which the three pairs of strain sensors are placed need not be located at constant intervals about the circumferential direction of the pin hole, and at least one pair of strain sensors may be placed at a location that is 90° to 180° relative to a setting position of another pair of strain sensors. This is because the measurement accuracy deteriorates if all the sensor pairs are concentrated and placed at 0° to 90°. However, it is desirable to avoid placement in which the angle between any two pairs among three pairs of strain sensors is 90°, considering a case where the cross-sectional shape of the pin body 1 deforms due to a load being applied to be vertically asymmetric in the load direction. These reasons are explained in detail in (Principle of Occurrence of Errors and Principle of Error Avoidance) that are described in the following. Also, placement of each strain sensor provided to the shearing strain generating portion 1A and each strain sensor provided to the shearing strain generating portion 1B need not be the same.

<Principle of Occurrence of Errors and Principle of Error Avoidance>

A load whose direction changes from moment to moment along with the progress of work acts on a turning shaft of a working machine. In the following, a principle of occurrence of measurement errors and tendency of errors that occur in a case where a load whose direction changes acts on a pin-type load cell that is a substitute of a turning shaft, and a reason why measurement errors can be avoided by providing three pairs of or three strain sensors are explained.

Figure 8:
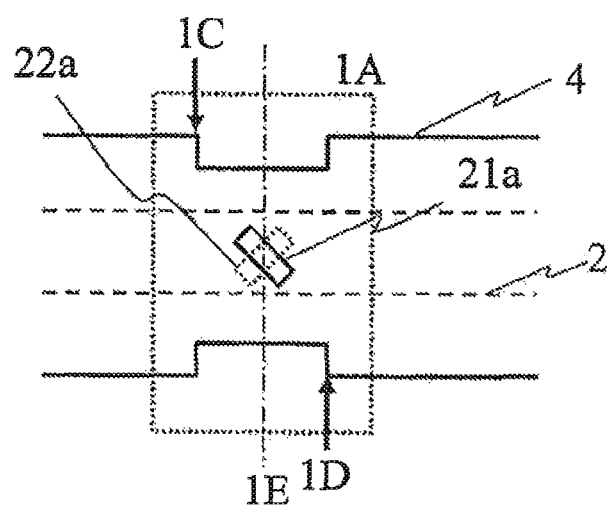
FIG. 8 is an enlarged view of a shear deformation generating portion of a pin-type load cell according to an embodiment.

FIG. 8 is an enlarged view of the shear deformation generating portion 1A of the pin-type load cell 4. In the pin-type load cell 4, the strain sensors 21a, 22a are provided at an intermediate position 1E (measurement point) between a load point 1C and a support point 1D and to the inner wall of the pin hole 2. The strain sensors 21a, 22a detect extension and contraction near the measurement point in the 45°-direction relative to the axial direction, and output the difference between output values of two pieces of the strain sensors 21a, 22a placed to be opposite to each other as shearing strain. If the cross-sectional shape of the pin-type load cell 4 does not change, and only shear deformation acts on the strain sensors 21a, 22a, the strain sensors 21a, 22a detect shearing strain due to a component of a load that acts on the pin-type load cell 4 in a direction corresponding to a sensor mounting surface.

Figure 9:
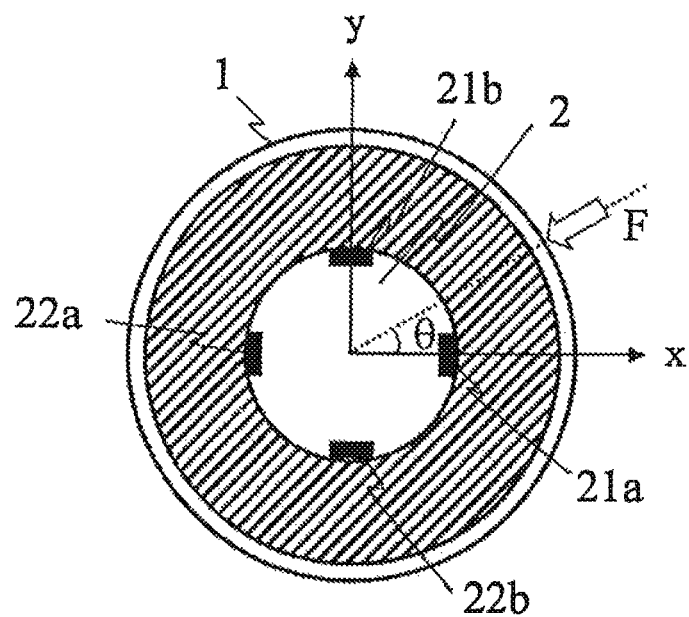
FIG. 9 is a horizontal cross-sectional view of a shearing strain detecting unit of a pin-type load cell according to a conventional example.

Next, a pin-type load cell 40 according to a conventional example in which two pairs of strain sensors (21a, 22a) and (21b, 22b) are placed at constant intervals as shown in FIG. 9 is considered. When a load with magnitude F acts on this pin-type load cell 40 from the direction θ, output values Sx and Sy of the strain sensor pair (21a, 22a) provided in the 0°-direction and the strain sensor pair (21b, 22b) provided in the 90°-direction are obtained as follows theoretically.

[Equation 3]

$$Sx = \alpha F \sin\theta$$

$$Sy = \alpha F \cos\theta \qquad (3)$$

Here, α is a constant that represents sensitivity of a strain sensor for a load. Force Fx in the x-axis direction and Fy in the y-axis direction can be calculated by multiplying the output values Sx, Sy of each pair of sensors with 1/α.

Figure 10A:
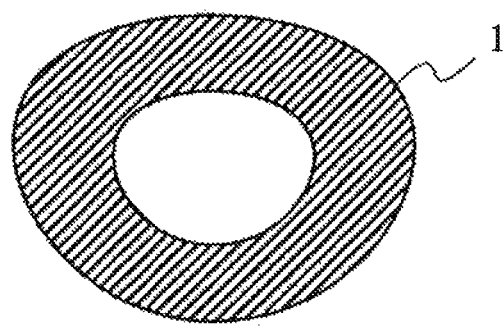
FIGS. 10A-10C are views for showing changes in the cross-sectional shape of a pin-type load cell when a load is applied thereto according to a conventional example, in which FIG. 10A corresponds to a cross-sectional shape of the pin-type load cell at a load point 1C shown in FIG. 8, FIG. 10B corresponds to a cross-sectional shape of the pin-type load cell at a measurement point 1E shown in FIG. 8, and FIG. 10C corresponds to a cross-sectional shape of the pin-type load cell at a support point 1D shown in FIG. 8.
Figure 10B:
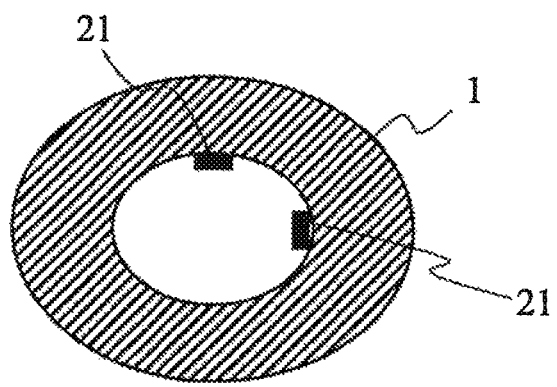
Figure 10C:
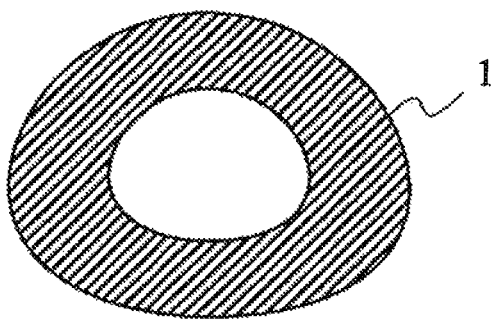

Meanwhile, the cross-sectional shape of the actual pin body 1 is deformed as shown in FIG. 10 when a load is applied due to influence of dimensional tolerance or the like of the pin hole 2 and a pin mounting portion. FIG. 10(*a*), FIG. 10(*b*), and FIG. 10(*c*) are enlarged views showing deformation of the cross-sectional shapes at the load point 1C, the measurement point 1E, and the support point 1D, respectively. As is obvious from these figures, deformations at the load point 1C and the support point 1D are vertically asymmetric due to influence of a load. Paying attention to the cross-sectional shape at each point, the cross-sectional shape at the load point 1C becomes smaller at its upper portion and larger at its lower portion, and conversely, the cross-sectional shape at the support point 1D becomes larger at its upper portion and smaller at its lower portion. In such a case, a detection value of the strain sensor 21 includes strain occurring due to the above-described asymmetric deformation as well as strain due to shear deformation. Also, because this strain due to asymmetric deformation of the cross-sectional shape varies depending on a relationship between the direction of action of a load and a sensor position, the magnitude of influence due to the asymmetric deformation of the cross-sectional shape changes depending on the direction of action of the load, and if a load value is calculated by using a calibrated value of a strain sensor in a certain direction of action of the load, a measurement error is generated when the direction of action of the load changes. Accordingly, when the cross-sectional shape of the pin body 1 is deformed vertically asymmetrically due to a load, the load F that acts on the pin body 1 and its direction of action cannot be obtained based on the output values Sx, Sy (see Equation 3) of the strain sensor pair (21*a*, 22*a*) and the strain sensor pair (21*b*, 22*b*) that are provided in the 0°-direction and the 90°-direction of the pin body 1, respectively.

Figure 11A:
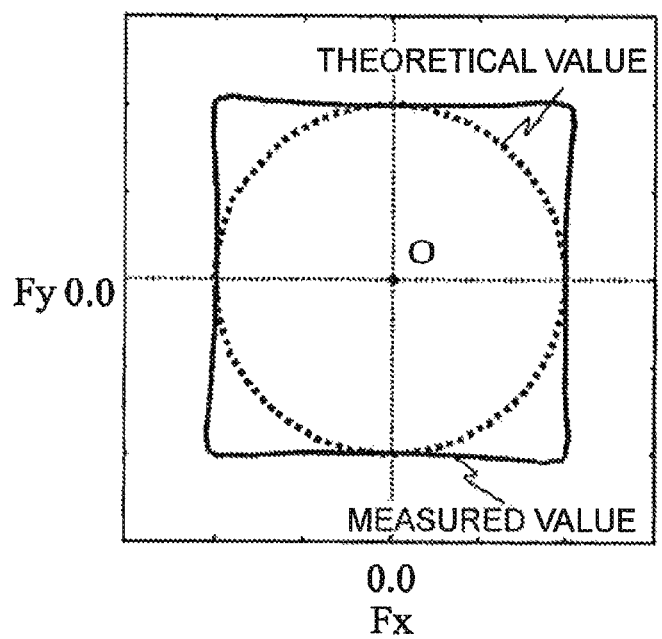
Figure 11B:
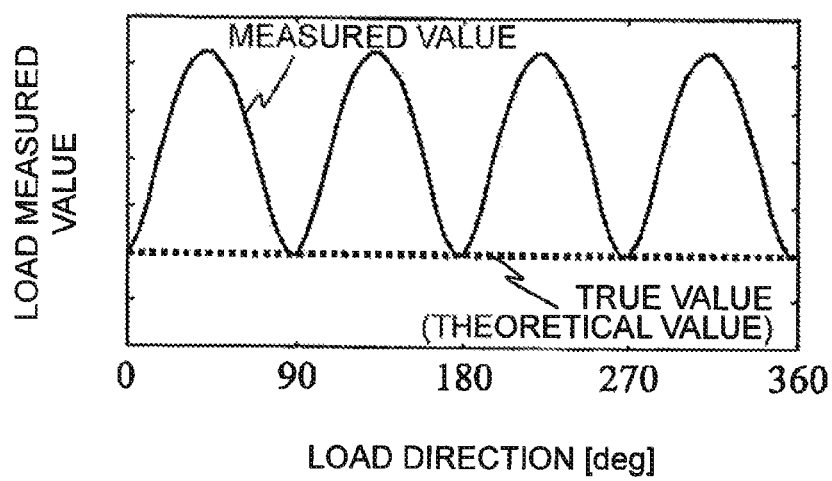

FIG. 11 shows a tendency of theoretical values and measured values of a load in the x-axis direction and the y-axis direction when the direction of action of the load is changed from 0° to 360°. FIG. 11(*a*) is a graph in which orientation of a straight line passing through the origin O indicates a load direction, and distance from the origin O indicates a load measured value, and FIG. 11(*b*) is a graph whose horizontal axis indicates a load direction and vertical axis indicates a load measured value. As is obvious from these figures, load measurement errors change depending the directions of action of the load, and they tend to be especially large in the directions of 45°, 135°, 225° and 315°. Also, the load calculated values tend to be minimum values in the directions of 0°, 90°, 180°, 270°. That is, if strain sensor calibration results acquired by using loads in the 0°-direction and the 90°-direction are used, errors always occur in the positive direction. The magnitude of load measurement errors varies depending on rigidity of a pin, that is, the quality material of or the outer diameter of the pin, and the pin hole diameter, and when the pin hole diameter is small, the magnitude decreases, but the relationship between the direction of action of a load and the magnitude of errors always shows tendency that is similar to the above-described tendency.

Accordingly, load measurement errors can be made small if measurement can be performed by avoiding the directions of 45°, 135°, 225° and 315°, and the neighborhood thereof that are likely to be influenced by asymmetric deformation of the cross-sectional shape and at which measurement errors become large. That is, in a case where the three pairs of or three strain sensors are placed in the circumferential direction of the pin body 1 as in the pin-type load cell 4 shown in FIG. 7, by installing at least one pair of strain sensors at locations of 90° to 180° relative to a setting position of another one pair of strain sensors, and avoiding placement in which the angle between any two pairs among three pairs of strain sensors is 90°, at least two pairs of or two strain sensors can be made less likely to be influenced by deformation of the pin body 1 even when a load acts on the pin body 1 from any direction. Therefore, highly accurate load measurement becomes possible by calculating a load that acts on the pin body 1 based on detection signals of these two pairs of or two strain sensors.

<Load Calculating Unit>

As shown in FIG. 6, the load calculating unit 30 is configured with: an input unit 31 that receives an input of a detection signal of the shearing strain detecting units 20; a calculating unit 32 that calculates three types of the magnitude of a load applied to the pin body 1 that are measured by different combinations of strain sensor pairs by using detection signals of two pairs of strain sensors selected from among three pairs of strain sensors; a selecting unit 33 that selects a combination that brings about the smallest calculated magnitude of a load from among the three types of combinations of strain sensors; and an output unit 34 that outputs the loads Fx, Fy in two axial directions that are calculated by the selected strain sensors. This load calculating unit 30 can be configured with a microcomputer or the like. It should be noted that the gist of the present invention is that as long as a calculating unit and a selecting unit are provided to the load calculating unit 30, it is possible to adopt a configuration in which the selecting unit that selects a strain signal input to the input unit 31 is placed at a former stage, and the calculating unit that calculates the loads Fx, Fy in two axial directions according to the selected strain signal is placed in a latter stage.

As methods of selecting two pairs from among the three pairs of strain sensors shown in FIG. 7 to calculate a load, there are three possible combinations to be used: the strain sensor pair (21*a*, 22*a*) and the strain sensor pair (21*b*, 22*b*); the strain sensor pair (21*b*, 22*b*) and the strain sensor pair (21*c*, 22*c*; and the strain sensor pair (21*a*, 22*a*) and the strain sensor pair (21*c*, 22*c*). As mentioned above, a load measurement error necessarily occurs in the positive direction if a calibrated value derived by using detection values when a load is applied to each strain sensor from the 0°-direction and the 90°-direction. Accordingly, a combination of strain sensor pairs that brings about the smallest measurement error is one that brings about a load value that is the smallest among three load values each of which is calculated by using detection signals of two pairs of strain sensors. That is, if Fab is the smallest among the load value Fab calculated by using the strain sensor pair (21*a*, 22*a*) and the strain sensor pair (21*b*, 22*b*), the load value Fbc calculated by using the strain sensor pair (21*b*, 22*b*) and the strain sensor pair (21*c*, 22*c*), and the load value Fac calculated by using the strain sensor pair (21*a*, 22*a*) and the strain sensor pair (21*c*, 22*c*), the strain sensor pair (21*a*, 22*a*) and the strain sensor pair (21*b*, 22*b*) are a combination of sensors that brings about the smallest measurement error. Accordingly, the load calculating unit 30 calculates a load value of each of the three combinations, selects a combination that brings about the smallest calculated load value as the best combination, and handles the load value calculated by using the combination as a load calculated value. When the mounting position of each pair of sensors is θa, θb, and θc, respectively, relative to the x-axis of the pin-type load cell 4, load values in the x-axis direction and the y-axis direction of each combination are calculated as follows.

[Equation 4]

$$Fabx = -\frac{F_a \cos\theta_b - F_b \cos\theta_a}{\sin(\theta_b - \theta_a)}$$

$$Faby = \frac{F_a \sin\theta_b - F_b \sin\theta_a}{\sin(\theta_b - \theta_a)}$$

$$Facx = -\frac{F_a \cos\theta_c - F_c \cos\theta_a}{\sin(\theta_c - \theta_a)}$$

$$Facy = \frac{F_a \sin\theta_c - F_c \sin\theta_a}{\sin(\theta_c - \theta_a)}$$

$$Fbcx = -\frac{F_b \cos\theta_c - F_c \cos\theta_b}{\sin(\theta_c - \theta_b)}$$

$$Fbcy = \frac{F_b \sin\theta_c - F_c \sin\theta_b}{\sin(\theta_c - \theta_b)}$$

(4)

Here, Fa, Fb and Fc are outputs of respective pairs of sensors after being converted into the dimension of force, and are values that are calculated by multiplying a difference between sensor outputs of two pieces of sensors forming each pair of sensors with a calibrated value of strain sensors. The magnitude of load values Fab, Fac, Fbc can be calculated as follows.

[Equation 5]

$$Fab = \sqrt{Fabx^2 + Faby^2}$$

$$Fac = \sqrt{Facx^2 + Facy^2}$$

$$Fbc = \sqrt{Fbcx^2 + Fbcy^2}$$

(5)

The load calculating unit 30 calculates the loads F1Ax, F1Ay that act on the shear deformation generating portion 1A as follows based on the load calculated value of each combination.

[Equation 6]

$$F1Ax = \begin{cases} Fabx & (\text{if } \min(Fab, Fac, Fbc) = Fab) \\ Facx & (\text{if } \min(fab, Fac, Fbc) = Fac) \\ Fbcx & (\text{if } \min(Fab, Fac, Fbc) = Fbc) \end{cases}$$

$$F1Ay = \begin{cases} Faby & (\text{if } \min(Fab, Fac, Fbc) = Fab) \\ Facy & (\text{if } \min(fab, Fac, Fbc) = Fac) \\ Fbcy & (\text{if } \min(Fab, Fac, Fbc) = Fbc) \end{cases}$$

(6)

Similar arithmetic operations are performed also for the shear deformation generating portion 1B, and loads F1Bx, F1By that act on the shear deformation generating portion 1B are calculated. The load calculating unit 30 calculates loads F4x, F4y that act on the pin-type load cell 4 as the sum of the load value detected in the shear deformation generating portion F1A and the load value detected in the shear deformation generating portion F1B, and outputs them as the load calculated values Fx, Fy.

[Equation 7]

$$Fx = F1Ax + F1Bx$$

$$Fy = F1Ay + F1By$$

(7)

Accordingly, the magnitude F of a load that acts on the pin-type load cell 4 is obtained by the following equation.

[Equation 8]

$$F = \sqrt{Fx^2 + Fy^2}$$

(8)

Figure 12A:
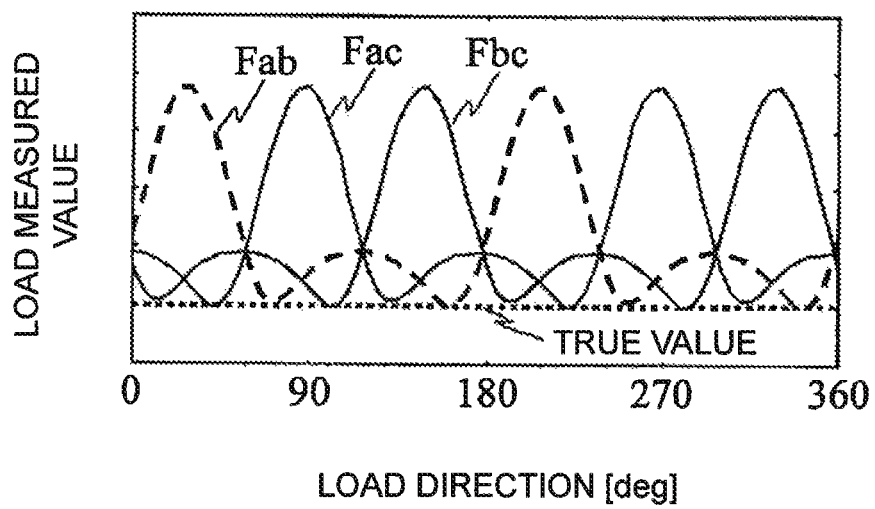
Figure 12B:
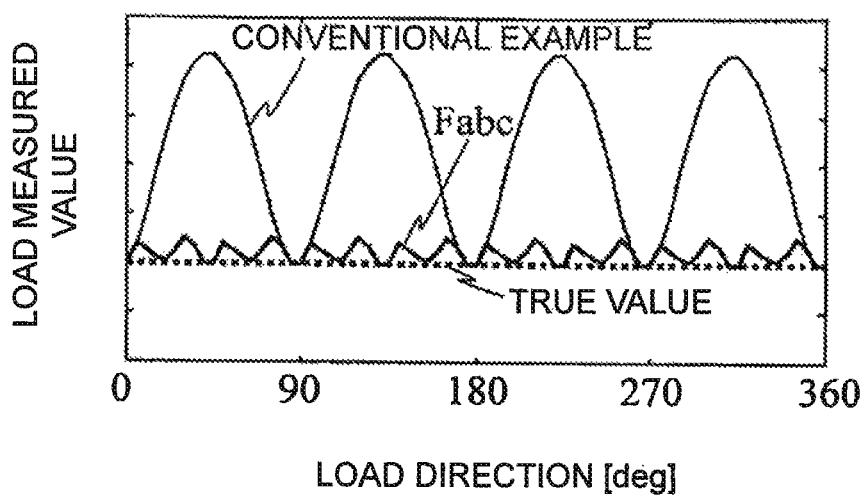

FIG. 12(a) is a figure that shows Fab, Fac, and Fbc obtained when the direction in which a load acts is changed in the pin-type load cell 4 according to the present embodiment, and FIG. 12(b) is a figure that shows the load calculated value Fabc. As shown in the figures, by placing three pairs of sensors, calculating loads by using two pairs among them, and selecting a combination that brings about the smallest load calculated value among all the combinations of sensors as the best combination, errors can be significantly suppressed as compared with a case where the configuration of the conventional example shown in FIG. 9 is used. Although large errors occur when the direction of action of a load is near 45°, 135°, 225° and 315° in the conventional example, it can be known that in the configuration of the present invention, errors are kept small even in such directions of action of a load, and highly accurate measurement can be performed regardless of the direction of action of a load.

<Variants>

Although the above-described embodiment shows an example in which three pairs of the strain sensors 21 are provided respectively to the shearing strain generating portions 1A, 1B, three is a minimum number so that two pairs or more of sensors that are less influenced by the above-mentioned asymmetric cross-sectional deformation always exist, and a larger number of sensor pairs may be provided. Also in a case where the number of sensor pairs is large, loads are calculated for all the possible combinations of two pairs similarly to the above-described case of three pairs, and a combination that brings about the smallest calculated value is selected as a best combination, and is used for calculation of Fx, Fy. By placing a further larger number of sensor pairs, sensors that are further less influenced by asymmetric cross-sectional deformation can be selected, and load calculation can be made further highly accurate.

Figure 13:
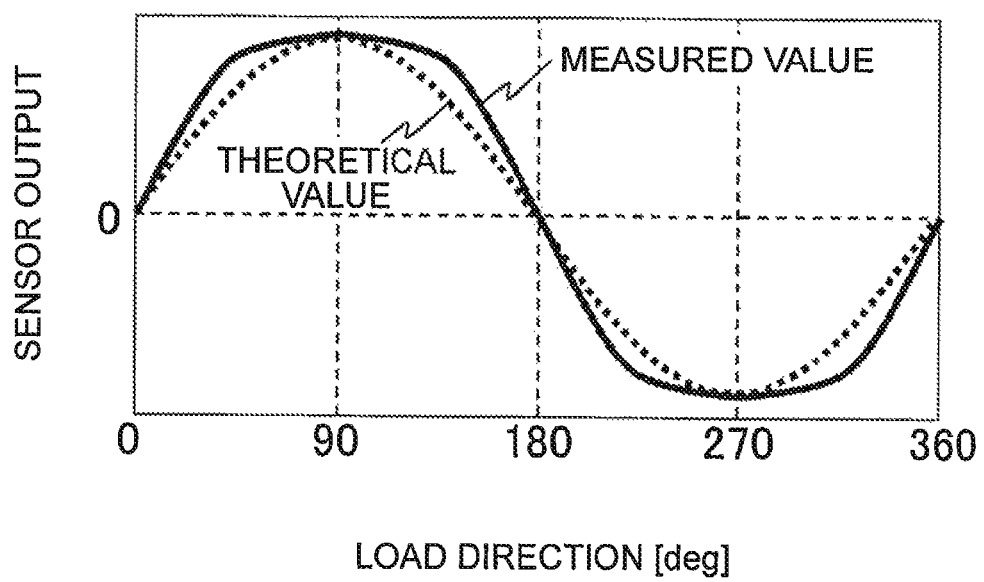
FIG. 13 is a figure that shows a relationship between theoretical values and measured values of a sensor output that are obtained when the load direction relative to the mounting position of a strain sensor is changed from 0° to 360°.

Also, the above-described embodiment shows a method in which the direction of action of a load is unknown, and sensors that are less influenced by asymmetric deformation are selected based on output values of the shearing strain detecting units 20 and are used for load calculation, but in a case where the direction of action of a load is known, it may be configured such that the angles between the direction of action of the load and sensors are calculated by using information on the direction of action of the load, and sensor pairs that are placed at positions that are more influenced by a change in the cross-sectional shape of the pin body are avoided based on this angular information, and two pairs that are less influenced by the change in the cross-sectional shape are selected, and used for load calculation. FIG. 13 shows a relationship between theoretical values and measured values of a sensor output that are obtained when the load direction relative to the mounting position of a strain sensor is changed from 0° to 360°. Differences between the theoretical values and the measured values shown in FIG. 13 correspond to influence of cross-sectional deformation of a pin body, but this magnitude varies depending on angles between the direction of action of a load and the sensor mounting position. Accordingly, by using angles between the direction of action of the load and sensors, two pairs that are less influenced by the cross-sectional deformation of the pin body can be selected from among the three pairs of sensors. Also, as mentioned above, in general, influence of cross-sectional deformation of a pin body tends to occur near 45°, 135°, 225° and 315° relative to a load direction. Accordingly, in general, it may be configured such that two pairs of sensors whose angles relative to the direction of action of the load are farthest from 45°, 135°, 225° and 315° are selected, and used for load calculation. Examples where the direction of action of a load is known include a case where working force is limited to the direction of gravitational force from among cases where pin-type load cells are applied to measurement of loads that act on an attachment of a working machine. In this case, the direction of a load that acts on a pin-type load cell can be calculated by deriving an angle between the pin-type load cell and the direction of gravitational force from an inclination angle sensor, an angle sensor or the like.

Also, although in the configuration in the above-described embodiment, strain sensors are provided to the inner wall of the pin hole 2 as the shearing strain detecting units 20, the shearing strain detecting units 20 only have to able to detect shearing strain of the shear deformation generating portions 1A, 1B, so it may be configured such that a strain sensor is provided in a concave portion formed in the outer periphery of the pin body 1, or it may be configured such that a strain detecting block is inserted into a pin hole, and a strain sensor is provided to a surface of the detecting block (for example, see JP-A No. S61-145426). In any case, the method of placing each pair of sensors and the method of calculating loads in the load calculating unit 30 may be similar to the above-described embodiment.

Also, although the above-described embodiment shows an example where strain sensors, as the shearing strain detecting units 20, are placed to be opposite to each other, instead of placing them on opposite surfaces, two pieces of strain sensor may be placed to be orthogonal to each other at the same position on the same surface. Also, when strain sensors that have functions that are equivalent to a function of calculating a difference of two pieces of strain sensors are used, three pieces of strain sensors may be placed. In this case, strain sensors may be placed such that at least one piece of a strain sensor is present at a position that is 90° or more away from the strain sensor 21A.

As mentioned above, because the working machine according to the embodiment is provided with a load detecting device that can highly accurately detect the magnitude and direction of a load that acts on a turning shaft (pin-type load cell) even when the direction of action of a load changes from moment to moment, the magnitude and direction of a load that acts on the attachment 123 can be detected highly accurately, and an operator or an operation manager can accurately grasp the state of the working machine. Therefore, it is possible to aim for improvement of work safety, and efficiency improvement of work and work management.

It should be noted that although the above-mentioned embodiment is explained by referring to an example where the magnitude and direction of a load that acts on the attachment 123 are detected by using the load detecting device, the gist of the present invention is not limited thereto, and for example, it is of course possible to detect the magnitude and direction of a load that acts on another part such as a coupling unit between the upperstructure 103 and the boom 110 or a coupling unit between the boom 110 and the arm 112 by using the load detecting device.

Also, the load detecting device according to the embodiments can be applied not only simply to a working machine, but also widely to load detection of machinery in general.

REFERENCE SIGN LIST

1: pin body
1A, 1B: shear deformation generating portion
1C: load point
1D: support point
1E: measurement point
2: pin hole
4, 4a, 4b: pin-type load cell
20: shearing strain detecting unit
21a, 22a, 21b, 22b, 21c, 22c: strain sensor (strain detecting unit)
30: load calculating unit
100: working machine
102: undercarrige
103: upperstructure
106: working device
110: boom
112: arm
112a: inclination angle sensor
115: attachment cylinder
116: first link
117: second link
118: link mechanism
123: attachment
123a: inclination angle sensor
140: turning shaft
140a: boom angle sensor
141: turning shaft
141a: arm angle sensor
142: turning shaft (arm-side pin)
142a: attachment angle sensor
144: turning shaft (link-side pin)
145: turning shaft
146: turning shaft
150: load measuring device
160: arithmetic operation device
161: display device

The invention claimed is:
1. A load detecting device comprising:
a pin-type load cell; and
a load calculating unit that calculates a load that acts on the pin-type load cell according to a detection signal output of the pin-type load cell, wherein
the pin-type load cell includes a pin body provided with a pin hole in an axial direction, and three or more pairs of or three or more strain detecting units placed in a circumferential direction of the pin body, and
the load calculating unit includes a selecting unit that selects, from among the three or more pairs of or three or more strain detecting units, a strain detecting unit that is less influenced by a change in a cross-sectional shape of the pin body, and a calculating unit that calculates a load that acts on the pin body based on a detection signal output of the strain detecting unit selected by the selecting unit.

2. The load detecting device according to claim 1, wherein the strain detecting unit detects a shearing strain at a mounting location.

3. The load detecting device according to claim 1, wherein the three or more pairs of strain detecting units are each a pair of two strain sensors placed at opposite positions via a shaft center of the pin body.

4. The load detecting device according to claim 1, wherein at least one pair of or one strain detecting unit is installed at a location that is 90° or more away from a setting position of a particular one pair of or one strain detecting unit from among the three or more pairs of or three or more strain detecting units.

5. The load detecting device according to claim 1, wherein the load calculating unit selects, from among the three or more pairs of or three or more strain detecting units, two pairs of or a group of two strain detecting units that bring about a smallest load calculated value, and calculates loads that act in an x-axis direction and a y-axis direction that is orthogonal thereto of the pin body according to detection signal outputs of the selected two pairs of or two strain detecting units.

6. The load detecting device according to claim 1, wherein the load calculating unit selects, from among the three or more pairs of or three or more strain detecting units, a strain detecting unit that is less influenced by a change in a cross-sectional shape of the pin body by using information on a direction of action of a load, and calculates a load according to an output of the selected strain detecting units.

7. The load detecting device according to claim 6, wherein the load calculating unit selects two pairs of or two strain detecting units whose angles relative to the direction of action of the load are farthest from 45°, 135°, 225°, and 315°, and calculates the load that acts on the pin body based on a detection signal output of the selected two pairs of or two strain detecting units.

8. A working machine, wherein a coupling unit of a mechanism member is joined by using the pin-type load cell according to claim 1.

9. The working machine according to claim 8, the working machine comprising: a undercarrige; an upperstructure mounted on an upper portion of the undercarrige; a working device mounted freely turnably on the upperstructure; an attachment mounted on a tip of the working device via a turning shaft; a posture detecting unit that detects a posture of the working machine; an arithmetic operation device that performs arithmetic operation to determine a load that acts on the attachment; and a display device that displays the load that acts on the attachment, wherein
a coupling unit between the working device and the attachment is coupled by using the pin-type load cell,
the arithmetic operation device calculates a load applied to the attachment based on an output of the posture detecting unit and the pin-type load cell, and
the display device displays magnitude and a direction of a load based on an output result of the arithmetic operation device.

* * * * *